(12) United States Patent
Bryden et al.

(10) Patent No.: US 7,125,437 B2
(45) Date of Patent: Oct. 24, 2006

(54) METHOD AND APPARATUS FOR ENHANCED PARTICLE COLLECTION EFFICIENCY

(75) Inventors: Wayne A. Bryden, Ellicott City, MD (US); Peter F. Scholl, Silver Spring, MD (US); Micah A. Carlson, Baltimore, MD (US); Michael P. McLoughlin, Sykesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 20 days.

(21) Appl. No.: 10/473,530

(22) PCT Filed: Apr. 14, 2003

(86) PCT No.: PCT/US03/11479

§ 371 (c)(1),
(2), (4) Date: Jun. 15, 2004

(87) PCT Pub. No.: WO03/089907

PCT Pub. Date: Oct. 30, 2003

(65) Prior Publication Data

US 2005/0000358 A1 Jan. 6, 2005

Related U.S. Application Data

(60) Provisional application No. 60/373,054, filed on Apr. 16, 2002.

(51) Int. Cl.
*G01N 1/00* (2006.01)
*B01D 53/14* (2006.01)

(52) U.S. Cl. .............................. 95/29; 95/149; 96/243; 96/389; 96/413; 73/28.01; 73/31.03; 73/863.22

(58) Field of Classification Search .................. 95/29, 95/149, 214, 216; 96/243, 389, 413; 55/DIG. 14, 55/DIG. 25; 73/28.01, 28.04, 28.05, 31.02, 73/31.03, 863.12, 863.22
See application file for complete search history.

(56) References Cited

U.S. PATENT DOCUMENTS

| 3,380,584 | A |   | 4/1968  | Fulwyler |
|-----------|---|---|---------|----------|
| 4,059,419 | A | * | 11/1977 | Ross ............................. 95/214 |
| 4,120,670 | A | * | 10/1978 | Pircon ........................... 95/216 |
| 4,280,823 | A |   | 7/1981  | Szonntagh |
| 4,329,316 | A | * | 5/1982  | Wladimiroff et al. .......... 422/52 |
| 4,378,976 | A | * | 4/1983  | Rush ............................... 95/29 |
| 4,767,524 | A | * | 8/1988  | Yeh et al. .................... 209/143 |
| 5,298,967 | A | * | 3/1994  | Wells ........................... 356/336 |
| 6,156,212 | A | * | 12/2000 | Rader et al. ................ 210/788 |
| 6,506,345 | B1 |  | 1/2003  | Lee et al. |
| 6,520,034 | B1 | * | 2/2003  | Masquelier et al. ...... 73/863.21 |
| 2002/0134137 | A1 | | 9/2002 | Ondov et al. |

* cited by examiner

*Primary Examiner*—Frank M. Lawrence
(74) *Attorney, Agent, or Firm*—Francis A. Cooch

(57) ABSTRACT

A method and apparatus for particle collection (30) that is characterized by co-aerosolizing fluids (62) into an air stream (34) containing the particles to be analyzed to significantly enhance their collection and identification efficiency is provided.

20 Claims, 2 Drawing Sheets

```
┌─────────────────────────┐
│   GUIDING AIR STREAM    │──12         10
│      ALONG PATH         │
└───────────┬─────────────┘
            ▼
┌─────────────────────────┐
│   GENERATING AQUEOUS    │──14
│        AEROSOL          │
└───────────┬─────────────┘
            ▼
┌─────────────────────────┐
│     CO-AEROSOLIZING     │
│  PARTICLES CARRIED BY   │──16
│       AIR STREAM        │
└───────────┬─────────────┘
            ▼
┌─────────────────────────┐
│  COLLECTING PARTICLES ON│──18
│    IMPACTION SURFACE    │
└───────────┬─────────────┘
            ▼
┌─────────────────────────┐
│  IDENTIFYING COAGULATED │──20
│        PARTICLES        │
└─────────────────────────┘
```

FIG. 1

METHOD AND APPARATUS FOR ENHANCED PARTICLE COLLECTION EFFICIENCY

CROSS REFERENCE TO RELATED APPLICATIONS

This application claims the benefit of prior filed U.S. Provisional Application 60/373,054, filed Apr. 16, 2002, the contents of which are incorporated herein by reference.

STATEMENT OF GOVERNMENTAL INTEREST

This invention was made with Government support under Contract No. MDA972-01-D-0005 awarded by the Defense Advanced Research Projects Agency. The Government has certain rights in this invention.

BACKGROUND OF THE INVENTION

1. Field of the Invention

The present invention generally relates to a sampling methodology. More particularly, the present invention is directed to a method and apparatus for improving capturing efficiency of airborne particulates and for providing immediate sample treatments which serve to enhance post-collection detection or identification systems.

2. Description of the Related Art

Particulate materials, dispersed in air, pose major threats to the health and safety of the populace. For example, the EPA has strict regulations for respirable dust particles, which may bear allergens capable of triggering severe allergic reactions such as, for example, asthma, in susceptible individuals. Building engineers are plagued with particulate materials, which may include microorganisms, causing sick building syndrome. The FAA and the military have requirements to detect minute particles for identification of explosive materials that may pose a threat to personnel. Finally, the threat of biological warfare requires systems that can efficiently collect and analyze minute quantities of airborne toxins, bacteria, and viruses. All of these critical applications require efficient concentration and collection of airborne particulate materials over a broad particle size range.

For optimum performance, the collection technology must rapidly provide the sample in a form that can be measured by the detector or sensor. For example, many biological sensors operate on a sample that is presented as a solution or suspension in water. For this type of detection device, the collection of sample must be gentle enough to minimize disruption of surface antigens present on the biological agents. On the other hand, sensors based on detecting chemical components of the particles generally require that the particles be disrupted in some manner to free the molecules of interest for detection. For these types of sensors, high-speed impaction onto solid phase surfaces, such as a metal plate coated with mineral oil, provides reasonable collection efficiency and the requisite disruption of the particulate into molecular components. Furthermore, for sensors that employ focused energy, such as a laser, in the detection scheme require that the sample be highly spatially localized on a surface. An example of this technology is laser ionization mass spectrometry. In this technique the particles in the air must be localized in a single sample spot of less than the diameter of the laser beam or ionization region to be effectively analyzed. In one embodiment, this area is required to be a circle with a diameter of the order of about one (1) millimeter.

A variety of sampling devices configured to separate and deliver the material to be tested by a sensor are designed based on how the sample is originated: whether it comes from air, liquid, solid objects, surfaces, or from human tissue. There are several issues that make sampling for biological agents particularly challenging. Firstly, some forms of analysis require living organisms for detection and, therefore, the collection technology must not "harm" the sample. Secondly, the target microbe is generally only one component of a complex matrix of biological elements and chemical compounds that may affect the detection process, so the sample must often be purified to some extent. Finally, the sample must be highly concentrated for a rapid analysis.

Among general types of sampling devices designed to accomplish one or more of these objectives that are of a particular interest within the context of the present invention are viable particle-size impactors and virtual impactors, cyclone samplers and bubblers. Each of these technologies is briefly described below.

A viable particle-size impactors typically has multiple stages. Each stage contains a number of precision-drilled orifices that are appropriate for the size of the particles to be collected in that stage, and orifice sizes decrease with each succeeding impactor state. Particles in the air enter the instrument and are directed towards the collection surface by the jet orifices. Any particle not collected by that stage follows the stream of air around the edge of the collection surface to the next stage. The collection plate is typically a petri dish with agar or other suitable growth medium.

A virtual impactor is similar to a viable particle-size impactor, but uses a collection probe instead of a flat plate as its impaction surface. Air flows through the collection probe and the collected particles are transported to other portions of the collector for additional concentration. By controlling the flow in the impactor, it is possible to adjust the cutoff size to the particles collected. By passing the collection probe airflow into successive virtual impactors, the particles can be concentrated many times the original air concentration before collection.

A cyclone is an inertial device that is commonly used in industrial applications for removing particles from large airflows. A particle-laden air stream enters the cyclone body and forms an outer spiral moving downward towards the bottom of the cyclone. Larger particles are collected on the outer wall due to centrifugal force. Smaller particles follow the airstream that forms the inner spiral and leave the cyclone through the exit tube.

A bubbler or impinger operates by drawing aerosols through a current inlet tube to create a jet. Usually the jet is submerged into the liquid contained in the sampler. As the air passes through the liquid, the aerosol particles are captured by the liquid surface at the base of the jet. In order to collect the smallest particles possible, the jet is typically made with a small critical orifice causing the flow to become sonic. Sampling small particles requires that due consideration be given to the variables that affect aerodynamic characteristics of the particulates, namely the size, number, randomness, and independence thereof. In particular, the size of the captured particulates can radically affect the collection efficiency of the cyclone and virtual impactor devices. The wetted-wall cyclone, and multi-stage virtual impactors feeding into true fluid impactors collect large volumes of air (on the order of about 1000 L/min), concentrate the respirable aerosol particles and impinge these into several milliliters of aqueous collection fluid. With proper tuning, these samplers provide high collection efficiency for particles greater than approximately one (1) micrometer in size. The collection efficiency drops precipitously for particles smaller than one micrometer. The central phenomenon exploited for operation of these devices is impaction of the particles, traveling at the proper velocity, onto a liquid collection surface. Upon the impact, the particles "splash down" into the fluid thereby minimizing particle bounce and reaerosolization into the exhaust airstream. While such samplers provide reasonably gentle capture, the relatively large volumes of collection fluid employed in this system lead to a dilution of the collected sample that makes sample cleanup and detection more difficult. Furthermore, the large volumes of collection fluid, when used for a long period of time, provides high logistics burden for fielded systems.

An alternative strategy, directed to overcome the disadvantages of the above-discussed impactors, is based on collection of sample by impaction onto a polymer tape. Developed at the Applied Physics Laboratory of Johns Hopkins University (JHU/APL), a sampling system, equipped with a polymer tape, features a two-stage virtual impactor particulate concentrator. The latter typically collects air at a rate of 800 L/min and outputs air that is concentrated by a factor of 20×for particles greater than approximately 1 um, at a rate of 15 L/min. The output air enters a five (5) jet true impactor that directs the particles toward the polymer surface where a fraction of them collect on the surface. Generally, however, a large fraction of the particles strike the surface of the tape, bounce off, and are reaerosolized into the airstream. These particles either deposit on an undesirable surface in the sampler or are lost in the exhaust air. The collection efficiency and spot localization for this approach have been found to be low.

To minimize particle bounce and therefore to enhance both the collection efficiency and spot localization, the sampling system designed by JHU/APL has been provided with a polymer tape coated with mineral oil, vacuum grease or an adhesive compound. However, this system requires an oily or sticky coating on the sample tape that tends to deposit on other mechanical motion components of the sampling system resulting in unacceptable performance. Furthermore, the collection efficiency for smaller particles such as viruses, certain types of bacteria and finely dispersed explosives still desires to be higher. Overall, the present technology may have the following deficiencies: (1) relatively low collection efficiency, particularly at small particle sizes; (2) harsh, dry environment in samplers that causes low viability for bacteria and viruses; and (3) poor focusing of deposited material.

Thus, despite the intense activity in the recent past to advance and develop bioaerosol samplers, a need remains for a method and an associated aerosol collector that would enhance particle collection efficiency for current samplers and particularly, for collectors utilizing solid-surface sample tapes. It would also be desirable to provide a method and apparatus characterized by improved identification of the collected particles.

SUMMARY OF THE INVENTION

The present invention, which addresses the needs of the prior art and meets the objects of the present invention, provides an apparatus and a method for increasing the aerodynamic size of airborne particles. More specifically, the basic concept underlying the present invention provides for the introduction of an aqueous aerosol into an air stream to increase the agglomeration of the carried particles, particularly small ones. As a consequence, the aerodynamic diameter of the aerosol particles is increased leading to the enhanced collection efficiency of a tape impactor.

Fluid droplets, contained in the aqueous aerosol and carried by the air stream towards the tape impactor, not only agglomerate with existing dry particulates making them larger and wet, thereby minimizing the bounce of the agglomerated particles, but also form small reservoirs of fluid on the impaction surface at the impaction location. Having such reservoirs is critical for the creation an environment beneficial for rapid growth or development of chemical or biological elements of interest immediately after the agglomerated particles have impinged upon the fluid contained in the reservoir. Thus, the formation of the fluid reservoir allows a variety of additives, introduced into the air stream and captured by the fluid, to chemically, biologically and/or mechanically provide beneficial conditions for the collected particles to be analyzed. Note, if not for the fluid reservoir, the introduced additives would rather bounce off the surface of the tape impactor and, thus, be ineffective for the intended purposes. Accordingly, results from reducing the inventive concept to practice indicate that the aqueous co-aerosolization protocol provides the following advantages: (1) enhanced collection efficiency of the airborne particulates; and (2) enhanced identification of the collected particles.

In accordance with a further aspect of the present invention, an apparatus configured to implement the inventive process is provided comprising a focusing mechanism allowing the aerosolized particle to be collected in a localized area. To materialize this concept of the invention, the focusing mechanism includes a structure traversed by the aerosolized air stream and configured to have a cross-section gradually reducing towards a targeted area. As a consequence, a relatively narrow outlet port of the focusing mechanism is directly juxtaposed with the targeted area difficult to miss as the aerosolized particles leave the outlet port. This feature of the invention even further enhances the collection efficiency of the apparatus configured in accordance with the inventive concepts.

It is, therefore, an object of the invention to provide a process and apparatus characterized by high collection efficiency for, among others, submicron particles.

Still another object of the invention is to provide a process and apparatus for rapidly sampling and processing a sufficient volume of ambient air to ensure that a relatively large number of specific microorganisms of interest are collected to form a representative sample over a short time period.

Still another object of the invention is to provide a process and apparatus for controllably generating an aerosol to increase the aerodynamic diameter of the particles of interest carried by an air stream.

Yet a further object of the invention is to provide an apparatus carrying out the inventive concept in a simple and reliable manner.

BRIEF DESCRIPTION OF THE DRAWINGS

The above and other objects, features and advantages will become more readily apparent from a detailed description of the preferred embodiment of the present invention accompanied by the following drawings, in which:

FIG. 1 is a diagrammatic view illustrating an inventive process; and,

DETAILED DESCRIPTION OF THE PREFERRED EMBODIMENTS

Figure 2:
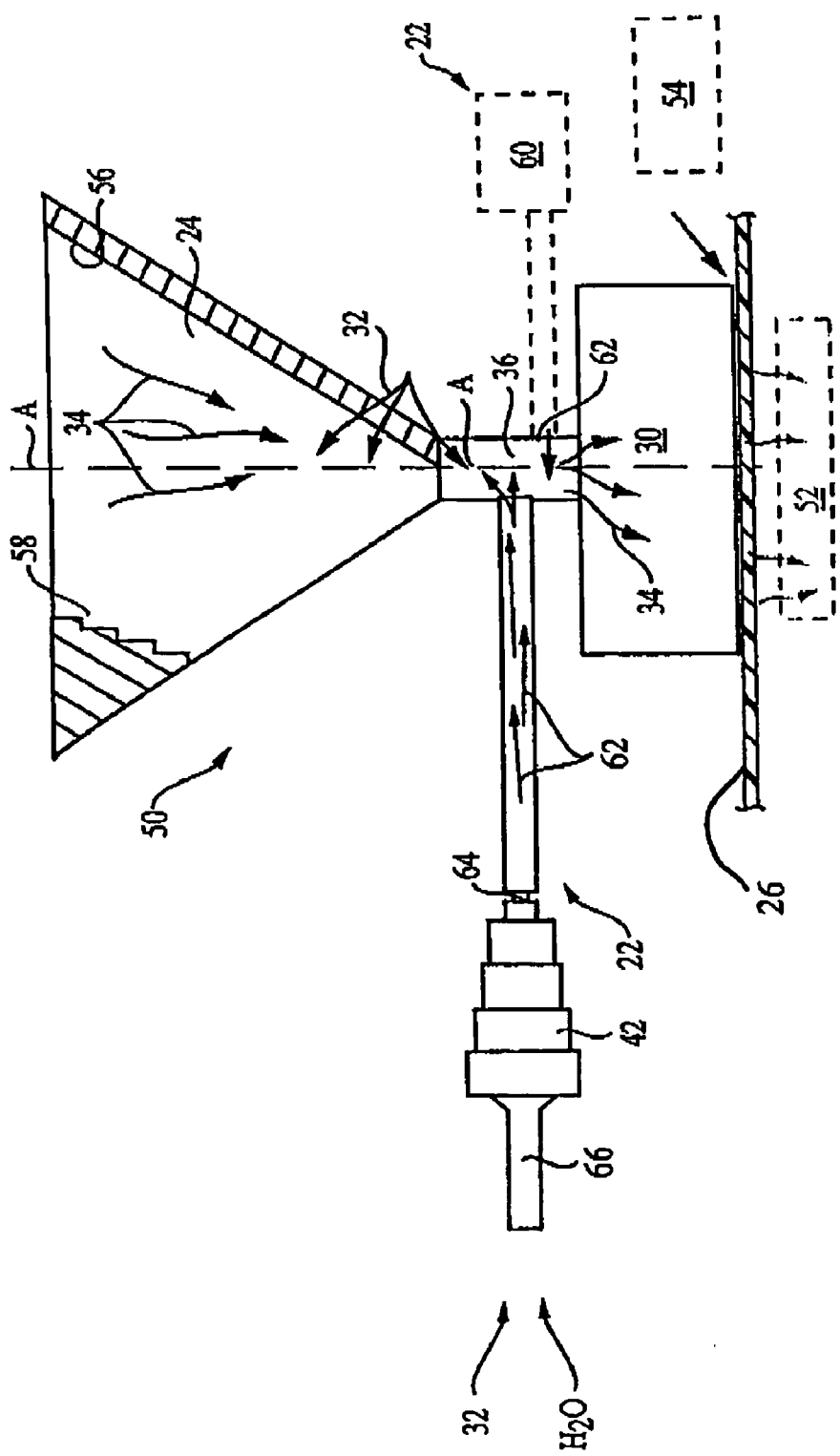
FIG. 2 is a schematic view of an inventive device configured to carry out the inventive process.

Referring to FIGS. 1 and 2, the inventive process 10 is configured to coagulate particles, particularly particles smaller than about 1 micrometer, with aqueous droplets to form larger particles that can be captured with much grater efficiency. Particularly, as denoted by box 12 in FIG. 1, an air stream 34 carrying particles to be analyzed is guided via a particle concentrator 24 (FIG. 2) towards an impaction-based sampler/collector 30 that can be a virtual air-air impactor or an air-surface (real) impactor. Finally, the concentrated air-stream is intercepted by an impaction surface 26, which, depending on a particle-analysis method, such as mass spectrometry, PCR, or culturing, may be a bare displaceable tape, metal surface, or a fluid reservoir, as will be discussed hereinbelow. As the air stream 34 advances along a flow path, an aerosol 62, generated at 14 by an aerosol generator 22, entrains the particles carried by the air stream. As a result of the aerosol introduction, particles carried by the air stream 34, even small particles having a size less than 1 micrometer, are co-aerosolized.

The co-aerosolization of the air stream triggers two particularly important mechanisms leading to the enhanced collection efficiency. First, aqueous droplets merge with small particles, which, thus, increase their aerodynamic diameter to form a target that can be relatively easily caught by the impaction surface 26. Second, since the enlarged particles hitting the surface 26 are wet, they do not bounce off the solid surface of the bare tape as easily as dry particles and remain "stuck" on the impaction surface. The combination of these mechanisms leads to an enhanced overall collection efficiency and sample spot localization with reference to the impaction surface 26, particularly in case of the bare tape or any other solid surface made from, for example, metal, as indicated by box 18 in FIG. 1.

The fluid co-aerosolization provides an enhanced capability for sample collection for a variety of analytical methods including, but not limited to a mass spectrometry based detection system 20 (FIG. 1), which is disclosed in U.S. application Ser. No. 10/030,396, filed Jan. 8, 2002, the contents of which are incorporated herein by reference. Briefly, the detection system 20 may comprise a laser configured to ionize the collected particulates (sample) from the tape located adjacent to a vacuum interface of mass spectrometer. Note, however, the inventive method can be applied to nearly all types of particulate collection including those that utilize a liquid impaction surface. The inventive method, carried out by an apparatus, as shown in FIG. 2, enhances the sample collection efficiency and spot localization that at least one order of magnitude higher than uncoated polymer substrates. Another benefit of implementing the aqueous co-aerosolization protocol is that the solid impaction surface 26, such as the tape, is mechanically easy to handle.

Furthermore, as the agglomerated aerosol particles continue impacting upon the surface of the solid impaction surface 26, a small pool of standing liquid droplets is formed on its surface. Thus, the fluid co-aerosolization creates a specific environment that chemically, biologically or even mechanically improves collection identification or processing of the collected organisms, particles or sample. In particular, in accordance with one of the inventive concepts, a variety of co-aerosolized additives 32 are introduced into the air stream 34, which, after having impinged upon the fluid pool, tend to affect the collected particles. If the impaction surface 26 is a fluid reservoir, the co-aerosolized additives 32 can affect the particles carried by the air stream 34 even before the coagulated particles hit the liquid impaction surface.

Formation of the pool of standing liquid droplets, of course, can be realized by introducing a metered volume of liquid into the system 20 directly in the vicinity of the impaction surface 26. One of such locations can be the base of the impaction nozzle. As a result, instead of introducing a somewhat excessive amount of droplets upstream from the impaction surface and having them impact thereupon, which may cause the impacting droplets to bounce off the surface 26, the pool of standing droplets can be created right on this surface.

To better understand the above-disclosed phenomenon, it is worth recalling a typical particle-identification procedure, in which collected particles or a sample is mixed with a solution known to place the collected particles in better condition for immediate or rapid processing.

In culturing, for example, where a time is of the essence, a rapid growth of collected organisms can greatly improve the identification efficiency. To accomplish it, an additive such as, for example, broth medium, sugar water and the like, can be co-aerosolized and impacted with particles to accelerate a growth of organisms before or after the co-aerosolized particles are collected. In the case of the liquid impaction surface 26, the organisms of interest can be somewhat prepared for analysis while still advancing toward the impaction surface along the co-aerosolized air stream. For collection of viruses, the inherent aqueous environment surrounding the aerosolized particles tends to lead to organisms that can remain microbiologically viable.

Another example relates to mass spectrometry. It is desirable that certain components, such as salts typically contained in the pool of fluid and inhibiting the identification of the sample, be removed therefrom before the processing of the sample begins. In accordance with the inventive concept, a component capable of neutralizing salts and including, for example water or an acid, can be injected into the air stream 34 and co-aerosolized as the air stream advances toward the pool formed on the solid impaction surface 26. As a consequence of a subsequent chemical reaction, when the "purified" sample, collected on the bare tape, is further analyzed by the mass-spectrometer system, the sample is, at least, less inhibited by elements that, otherwise, would impede or be detrimental to the analytical process.

Once the collection of the coagulated particles is performed, the excess of the fluid accumulated on the solid impaction surface 26, formed as a porous membrane, is sucked in by a vacuum means 52 juxtaposed with the membrane's bottom. Alternatively, a blower 54 facing the bare tape can blow the excess of the fluid off this surface.

Thus, reducing inhibitors confounding the organisms or elements to be analyzed and/or creating a beneficial environment used for further detection in systems such as PCR or mass-spectrometry systems substantially reduces a number of preliminary steps leading to a final analytical stage. Note that although the incoming air stream is capable of drying the pool of fluid on the impaction surface 26, the pool is continuously replenished as new coagulated particles impinge upon the bare tape.

Turning to FIG. 2, an apparatus 50 configured to carry out the inventive method includes, as discussed above, impactor 30 traversed by the air stream 34 and configured to sample the particles carried by the air stream. Depending on the overall configuration of the apparatus 50, impactor 30 can be, for example, a single stage or multi-stage virtual impactor, and/or a real air-surface impactor. Regardless of the specific type and configuration, impactor 30 samples the particles entranced in the air stream 34 based on its geometry.

In accordance with one aspect of the invention directed to the enhancement of the localization of the samples, the apparatus 50 is provided with an aerodynamic focusing mechanism 24 located upstream from the impaction surface 26. The focusing mechanism can be located either upstream from the impactor 30, as shown in FIG. 2, or downstream therefrom as long as its configuration enhances the overall collection efficiency. In use, a relatively large air stream 34 traversing the virtual impactor can be channeled along a gradually narrowing air path defined by the geometry of guiding surface 56 of the focusing mechanism 24. A variety of geometrically different guiding surfaces of the focusing mechanism 24 can be utilized to direct the air stream 34 to the localized area of the solid or liquid impaction surface 26. For instance, the focusing mechanism 24 can have a smooth conical guiding surface 56 centered along an axis A-A and running into a relatively short cylindrical portion 36. Alternatively, the inner surface can be patterned to have, for example, a stepwise or cascading structure 58 leading to the portion 36. Critically, the air stream 34 is guided along the centerline or axis A-A. The location of aerodynamic focusing mechanism 24 can be changed so that is mounted directly upstream from the impaction surface 26. Note that the position of the components of the apparatus 50 relative to one another can be easily modified as long as the sampling and guiding characteristics of the apparatus meet the local requirements. For example, a virtual impactor can be positioned along the upstream of the air stream 34 and in flow communication with the focusing mechanism 24, which may be located directly downstream from the virtual impactor or is separated therefrom by a real impactor.

The presence of the focusing mechanism 24 in combination with lower particle velocities of the present method is also advantageous for liquid-based impaction-based surfaces or collectors since the latter would be provided with much smaller volumes of capturing fluid still catching the higher concentration of the particles. Hence, the present apparatus coupled with a fluid based collector is characterized by higher detection probability. Furthermore, the limited volumes of liquid greatly reduce the logistics burdens associated with these types of devices.

The development of the inventive method includes the utilization of the aerosol generator 22 mounted upstream from the impaction surface 26. Among a variety of methods and devices configured to generate an external aerosol are, for example, a standard nebulizer, a piezo-electric based nebulizing system and/or an inkjet style aerosol generator, which have been successfully implemented.

A standard nebulizer 60 uses a pressurized air stream to generate liquid particulates by initially aspirating a liquid out of a reservoir and blows the aspirated liquid against a surface to cause particulates contained in the liquid to shear apart. Entranced in a carrier fluid, generated by a pressurized source, the sheared particulates become aerosolized and delivered into the air stream 34 to co-aerosolize the particles of interest contained in the air stream 34. The location of the aerosol delivery into the air path 34 can vary. For example, as shown in FIG. 2, the aerosol 62 entrains the air stream while the latter flows along the narrow cylindrical portion 36 of the focusing mechanism 24. Another possible location of the injection is at an input plenum to the impactor 30. Alternative locations for the injection are between the air-air virtual impactor and the tape impactor 26 or between the stages of the multistage virtual impactor.

To improve control and prevent introduction of an unwanted volume of carrier fluid, a piezo-electric based nebulizing system has been used. While a variety of such systems are known, Sono-Tek MicroSpray™ nozzles have been particularly successful in the inventive apparatus 50. Focused parabolic or conical piezoelectric ultrasonic transducer 42 is a ceramic chip that acts as a capacitor while connected to a continuous wave power amplifier. The power amplifier (not shown) is driven through a sine wave cycle by a high frequency oscillator. The frequency of the oscillator is set by the known resonance frequency of the transducer causing positive displacement of the transducer. Formed centrally within the body of cone 42 is a small orifice 64 traversed by fluid, such as water. As shown in FIG. 2, when the fluid, driven by a positive displacement pump for field applications or a syringe pump 66 arrives at the tip of the cone 42, the latter vibrates to shear apart particulates. As a consequence, the fluid becomes the aerosol 62 having desired aerodynamic characteristics as it is injected into the air stream 34. One of the advantages of the piezo-electric base nebulizer is that it does not need a carrier gas. The liquid acts like a gas. Thus, there is no dilution of the gas stream, the phenomenon that may be observed during the use of the standard nebulizer 60. Still another advantage of the piezo-based electric nebulizer 42 is that the size of the droplet "sheared" off is dependent upon the frequency of the transducer. Therefore, the piezo-electric based nebulizer 42 provides simple control and reproducibility. Finally, various chemical constituents of the liquid are not destroyed separated by physical properties such as boiling point, density differences, or by vapor pressure. The latter feature is particularly important when the desired additives are introduced and co-aerosolized.

Addition of the additives 32 enhancing chemical, biological and/or mechanical characteristics of the particles of interest can be done directly by introducing the desired additives via the aerosolization generator 22. However, the additives 32 can be introduced or injected into the air stream 34 along any stretch of the flow path thereof subject to the efficient co-aerosolization of the additives.

While the invention has been disclosed with respect to preferred embodiments and illustrated without adhering to true dimensions, various changes can be added without departing from the scope of the invention as defined by the appending claims.

What is claimed is:

1. A method for particle collection comprising the steps of:
    guiding an air stream containing particles to be collected and analyzed toward an impaction surface; and
    introducing an aerosol containing aqueous droplets into the air stream upstream from the impaction surface to coagulate the particles with the aqueous droplets and to increase a size of the particles enhancing a collection efficiency of the coagulated particles on the impaction surface, wherein the introduction of the aerosol includes directing a pressurized stream of carrier gas against a reservoir containing a liquid, thereby aspiring the liquid out of the reservoir while shearing liquid particulates apart to aerosolize the aspired liquid before co-aerosolizing the particles in the air stream.

2. A method for particle collection comprising the steps of:
    guiding an air stream containing particles to be collected and analyzed toward an impaction surface; and
    introducing an aerosol containing aqueous droplets into the air stream unstream from the impaction surface to coagulate the particles with the aqueous droplets and to increase a size of the particles enhancing a collection efficiency of the coagulated particles on the impaction surface, wherein the introduction of the aerosol includes driving a selected liquid through a piezo-electric based element and vibrating the piezo-electric element at a desired frequency sufficient to shear apart liquid particulates to generate the aerosol as the liquid particulates traverse an outlet of the piezo-electric based element.

3. A method for particle collection comprising the steps of:
  guiding an air stream containing particles to be collected and analyzed toward an impaction surface;
  introducing an aerosol containing aqueous droplets into the air stream upstream from the impaction surface to coagulate the particles with the aqueous droplets and to increase a size of the particles enhancing a collection efficiency of the coagulated on the impaction surface;
  wetting the impaction surface as the coagulated particles impinge against the impaction surface to form a pool of liquid on the impaction surface configured to minimize bouncing of the coagulated particle off the impaction surface to enhance the collection efficiency; and
  selecting additives and co-aerosolizing the selected additives to create an environment in the air stream or in the pool of liquid on the impaction surface capable of mechanically, chemically or biologically modifying the coagulated particles to enhance identification of the collected coagulated particles, wherein the additives are so selected that the environment created in the air stream or in the pool of liquid allows accelerated growth of organisms to be cultured.

4. The method for particle collection comprising the steps of:
  guiding an air stream containing particles to be collected and analyzed toward an impaction surface;
  introducing an aerosol containing aqueous droplets into the air stream upstream from the impaction surface to coagulate the particles with the aqueous droplets and to increase a size of the particles enhancing a collection efficiency of the coagulated particles on the impaction surface;
  wetting the impaction surface as the coagulated particles impinge against the impaction surface to form a pool of liquid on the impaction surface configured to minimize bouncing of the coagulated particle off the impaction surface to enhance the collection efficiency; and
  selecting additives and co-aerosolizing the selected additives to create an environment in the air stream or in the pool of liquid on the impaction surface capable of mechanically, chemically or biologically modifying the coagulated particles to enhance identification of the collected coagulated particles, wherein the additives are so selected that the environment created in the pool of liquid is capable of reducing salts inhibiting further analysis of the collected coagulated particles.

5. The method of claims 1 or 2, further comprising the steps of:
  wetting the impaction surface as the coagulated particles impinge against the impaction surface to form a pool of liquid on the impaction surface configured to minimize bouncing of the coagulated particle off the impaction surface to enhance the collection efficiency; and
  removing an excess of liquid from the pool of liquid by either blowing the excess thereof off the impaction surface or by vacuuming the excess thereof from the pool of liquid.

6. The method of claims 1 or 2, further comprising identifying the collected coagulated particles in a mass spectrometer, PCR or a similar detection system.

7. The method of claims 1 or 2, wherein the air stream is guided through an impactor located upstream from the impaction surface, the impactor being selected from the group consisting of a virtual single stage impactor, a virtual multi-stage impactor, a real impactor and a combination thereof.

8. The method of claim 7, further comprising focusing the air stream entrained by the aerosol by guiding the air stream through a focusing mechanism located upstream from or downstream from the impactor.

9. The method of claim 8, wherein the air stream entrained by the aerosol is guided through a progressively narrowing guiding surface of the focusing mechanism directing the air stream towards a localized area on the impaction surface.

10. The method of claim 9, further comrising introducing the aerosol between the focusing mechanism and the impaction surface.

11. The method of claims 1 or 2, wherein the aerosolized aqueous droplets coagulate the particles having a size ranging from less than 1 micrometer to more than 1 micrometer.

12. An apparatus for collecting particles carried by an air stream, comprising:
  a guide configured to advance the air stream along a path;
  an impaction surface located downstream from the guide and configured to intercept the guided air stream and collect the particles;
  an aerosolization generator configured to create an aerosol entraining the air stream unstream from the impaction surface to coagulate with the particles so as the coagulated particles increase an aerodynamic diameter thereof to enhance collection efficiency of the impaction surface upon impinging the coagulated particles thereagainst; and a liquid reservoir in flow communication with the aerosolization generator, and a source of pressurized carrier gas aspiring the liquid out of the reservoir while shearing apart liquid particulates to create the aerosol.

13. An apparatus for collecting particles carried by an air stream, comprising:
  a guide configured to advance the air stream along a path;
  an impaction surface located downstream from the guide and configured to intercept the guided air stream and collect the particles;
  an aerosolization generator configured to create an aerosol entraining the air stream upstream from the impaction surface to coagulate with the particles so as the coagulated particles increase an aerodynamic diameter thereof to enhance collection efficiency of the impaction surface upon impinging the coagulated particles thereagainst, wherein the aerosolization generator includes a piezo-electric based nebulizer in flow communication with the guide and located unstream from the impaction surface; and
  a positive displacement pump or a syringe pump in flow communication with the piezo-electric based nebulizer including a focused parabolic or conical piezoelectric ultrasonic transducer operative to vibrate at a desired frequency to create liquid droplets having desired aerodynamic characteristics to agglomerate the particles upon injection of the aerosol into the guide.

14. The apparatus of claims 12 or 13, wherein the coagulated particle wet the impaction surface to form a small pool of liquid, the apparatus further comprising a source of additives introducible upstream from impaction surface into the air stream to create an environment capable of mechanically, chemically or biologically modifying the collected coagulated particles to enhance identification thereof.

15. The apparatus of claim 13, wherein the guide includes an impactor, the impactor being selected from the group consisting of a virtual single-stage impactor, a virtual multi-stage impactor, and a real impactor, and further includes a focusing mechanism in flow communication with the impactor and located upstream or downstream therefrom along the path to guide the air stream towards a localized area on the impaction surface.

16. The apparatus of claim 15, wherein the focusing mechanism has an inner surface tapering towards the impaction surface and being either smooth or cascaded to direct the air stream entrained with the aerosol towards the localized area on the impaction surface.

17. The apparatus of claim 15, wherein the aerosolization generator is attached either to an input plenum of the impactor or between the impactor and the impaction surface or between the multiple stages of the multi-stage impactor.

18. The apparatus of claim 15, wherein the impaction surface is either a displaceable bare tape or a liquid.

19. The apparatus of claim 14, further comprising a device juxtaposed with the impaction surface and operative to remove excess of the liquid in the pool.

20. The apparatus of claims 12 or 13, further comprising a laser mass spectrometer or a PCR operative to identify the coagulated particles collected on the impaction surface.

* * * * *